United States Patent
Roy et al.

(10) Patent No.: US 12,190,999 B2
(45) Date of Patent: Jan. 7, 2025

(54) SYSTEMS AND METHODS FOR PREDICTING POTENTIAL INHIBITORS OF TARGET PROTEIN

(71) Applicant: Tata Consultancy Services Limited, Mumbai (IN)

(72) Inventors: Arijit Roy, Hyderabad (IN); Sowmya Ramaswamy Krishnan, Hyderabad (IN); Navneet Bung, Hyderabad (IN); Gopalakrishnan Bulusu, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 404 days.

(21) Appl. No.: 17/137,001

(22) Filed: Dec. 29, 2020

(65) Prior Publication Data

US 2022/0084627 A1 Mar. 17, 2022

(30) Foreign Application Priority Data

Sep. 14, 2020 (IN) .............................. 202021039779

(51) Int. Cl.
  *G16B 25/10* (2019.01)
  *G16B 40/00* (2019.01)
  *G16B 50/30* (2019.01)

(52) U.S. Cl.
  CPC ............. *G16B 25/10* (2019.02); *G16B 40/00* (2019.02); *G16B 50/30* (2019.02)

(58) Field of Classification Search
  USPC .......................................................... 702/19
  See application file for complete search history.

(56) References Cited

U.S. PATENT DOCUMENTS

2022/0383992 A1* 12/2022 Triendl .................. G06N 3/047

OTHER PUBLICATIONS

"Autodock Vinal Manual." Center for Computational Structural Biology, 2010, vina.scripps.edu/manual/#installation. (Year: 2010).*

Shi, Tingting, et al. "A molecular generative model of ADAM10 inhibitors by using GRU-based deep neural network and transfer learning." Chemometrics and Intelligent Laboratory Systems 205 (2020): 104122. (Year: 2020).*

Wikipedia contributors. "Chemical similarity." Wikipedia, The Free Encyclopedia. Wikipedia, The Free Encyclopedia, Jul. 17, 2023. Web. Jul. 21, 2023. (Year: 2023).*

Gupta et al., "Generative Recurrent Networks for De Novo Drug Design", Molecular Informatics, NCBI, vol. 36, issue 1-2, pp. 1-10, 2017 Link: https://www.researchgate.net/publication/320813292_Generative_Recurrent_Networks_for_De_Novo_Drug_Design/link/5a2101e00f7e9b4d19282767/download.

Ramensky et al., "A novel approach to local similarity of protein binding sites substantially improves computational drug design results", Proteins Structure Function and Bioinformatics, NCBI, vol. 69, issue: 2, pp. 349-357, 2007 Link: http://www.rtcb.iitp.ru/PDF/17623865.pdf.

Merk et al., "De Novo Design of Bioactive Small Molecules by Artificial Intelligence", Molecular Informatics, NCBI, vol. 37, issue: 1-2, pp. Title Page and pp. 1-5, 2018 Link: https://www.researchgate.net/publication/322367205_De_Novo_Design_of_Bioactive_Small_Molecules_by_Artificial_Intelligence/link/5a56427e45851547b1bf12d5/download.

Howard et al., "Active site similarity between human and Plasmodium falciparum phosphodiesterases: considerations for antimalarial drug design", Journal of Computer-Aided Molecular Design, NCBI, vol. 25, issue: 8, pp. 753-762, 2011 Link: https://link.springer.com/article/10.1007/s10822-011-9458-5.

* cited by examiner

*Primary Examiner* — G. Steven Vanni
(74) *Attorney, Agent, or Firm* — FINNEGAN, HENDERSON, FARABOW, GARRETT & DUNNER, LLP

(57) ABSTRACT

Conventionally, deep learning-based methods have shown some success in ligand-based drug design. However, these methods face data scarcity problems while designing drugs against novel targets. Embodiments of the present disclosure provide systems and methods that leverage the potential of deep learning and molecular modeling approaches to develop a drug design pipeline, which can be useful for cases where there is limited or no availability of target-specific ligand datasets. Inhibitors of other proteins, structurally similar to the target protein are screened at the active site of the target protein to create an initial target-specific dataset. Transfer learning is implemented to learn features of target-specific dataset and design new chemical entities/molecules using a deep generative model. A deep predictive model is used predict docking scores of newly designed/identified molecules. Both these models are then combined using reinforcement learning to design new chemical entities with optimized docking score.

6 Claims, 9 Drawing Sheets

SYSTEMS AND METHODS FOR PREDICTING POTENTIAL INHIBITORS OF TARGET PROTEIN

PRIORITY CLAIM

This U.S. patent application claims priority under 35 U.S.C. § 119 to: India Application No. 202021039779, filed on Sep. 14, 2020. The entire contents of the aforementioned application are incorporated herein by reference.

TECHNICAL FIELD

The disclosure herein generally relates to drug development, and, more particularly, to systems and methods for predicting potential inhibitors of target protein.

BACKGROUND

Drug discovery is a time-, cost- and resource-intensive process. A drug undergoes several stages of development including hit identification, lead optimization, pre-clinical and clinical trials prior to its approval. Accelerating the initial phases of the drug discovery has the potential to save valuable time and cost invested in the downstream phases of the different steps.

The primary aim of drug design is to modulate the biological function of a specific target protein through identification of novel small molecules specific to the target protein of interest. Traditional drug design approaches have been able to explore only a small region of the chemical space, which encompasses approximately a billion drug-like small molecules. However, a vast expanse of the chemical space estimated to contain ~$10^{63}$ small molecules, still remains unexplored. With the potential of deep learning approaches, this gap in exploration can be addressed to design diversified and potential new chemical entities (NCEs) with desired drug-like properties. Further, the challenge is to develop methods which enable tailoring of small molecules against any target protein of interest. Such methods can remain unfazed by limited or no data availability for target proteins and can enable rapid discovery of potential drug-like molecules against emerging diseases.

Artificial intelligence (AI) and big data have shown a radical transformation in the accuracy and reliability of computational models, which are of paramount importance in critical fields of healthcare, including drug discovery. Deep neural network models are usually trained to learn feature representations from training data, which is commonly represented using the Simplified molecular input line entry system (SMILES) or molecular graphs for de novo drug design. With the learnt representation, neural networks can optimize multiple structural and physico-chemical parameters of relevance to drug discovery. Further, through memory-augmentation, the ability of deep learning models to design chemically valid molecules can be significantly improved. While there have been several advancements in the algorithms and applications of AI-based methods, the availability of data for protein-specific drug discovery and effective sampling of chemical space still remains as a challenge.

SUMMARY

Embodiments of the present disclosure present technological improvements as solutions to one or more of the above-mentioned technical problems recognized by the inventors in conventional systems.

For example, in one aspect, there is provided a processor implemented method for predicting potential inhibitors of a target protein. The method comprises: receiving, via one or more hardware processors, an input comprising the target protein; applying, a transfer learning technique via the one or more hardware processors, on a pre-trained generative model using a target protein specific dataset (TPSD) to obtain a target-specific generative model (TSGM) for the target protein; iteratively applying via the one or more hardware processors, a reinforcement learning (RL) technique on the target-specific generative model and a predictive model to obtain a set of target-specific small molecules, wherein each target-specific small molecule from the set of target-specific small molecules comprises one or more associated physico-chemical properties, wherein the predictive model is pre-trained using a protein dataset, and wherein the one or more associated physico-chemical properties for each target-specific small molecule from the set of target-specific small molecules are predicted by the predictive model; applying, via the one or more hardware processors, one or more filters on each target-specific small molecule from the set of target-specific small molecules to obtain a reduced set of target-specific molecules, wherein each molecule from the reduced set of target-specific molecules comprises one or more desired physico-chemical properties; and performing, via the one or more hardware processors, a virtual screening of the reduced set of target-specific molecules against the target protein to obtain a screened set of target-specific molecules, wherein the screened set of target-specific molecules serve as one or more potential inhibitors of the target protein.

In an embodiment, the target protein specific dataset (TPSD) is a curated target protein specific dataset (CTPSD) obtained by: obtaining a plurality of other proteins having one or more properties similar to one or more corresponding properties of the target protein; and curating a plurality of small molecules comprised in each of the plurality of other proteins to the target protein specific dataset (TPSD).

In an embodiment, the one or more properties similar to the one or more corresponding properties of the target protein comprise at least one of one or more sequence similarities, and a structural similarity (e.g., an active site conservation).

In an embodiment, the CTPSD comprises at least a subset of the plurality of other proteins, and wherein each protein from the subset of the plurality of other proteins comprises one or more small molecules.

In an embodiment, the one or more small molecules are associated with a docking score that is greater than or equal to a threshold score. In one embodiment, the docking score is computed using one or more methods.

In an embodiment, the one or more physico-chemical properties comprise at least one of a Synthetic Accessibility Score (SAS), a biological activity, a partition co-efficient (log P), a molecular weight, and a docking score.

In an embodiment, the set of target-specific small molecules is obtained based on a reward assigned to the target-specific generative model by the RL technique. In one embodiment, a binding affinity of the set of target-specific small molecules is increased based on the reward assigned to the target-specific generative model by the RL technique.

In another aspect, there is provided a processor implemented system for predicting potential inhibitors of a target protein. The system comprises: a memory storing instructions; one or more communication interfaces; and one or more hardware processors coupled to the memory via the one or more communication interfaces, wherein the one or more hardware processors are configured by the instructions to: receive an input comprising the target protein; apply a transfer learning technique on a pre-trained generative model using a target protein specific dataset (TPSD) to obtain a target-specific generative model (TSGM) for the target protein; iteratively apply a reinforcement learning (RL) technique on the target-specific generative model and a predictive model to obtain a set of target-specific small molecules, wherein each target-specific small molecule from the set of target-specific small molecules comprises one or more associated physico-chemical properties, wherein the predictive model is pre-trained using a protein dataset, and wherein the one or more associated physico-chemical properties for each target-specific small molecule from the set of target-specific small molecules are predicted by the predictive model; apply one or more filters on each target-specific small molecule from the set of target-specific small molecules to obtain a reduced set of target-specific molecules, wherein each molecule from the reduced set of target-specific molecules comprises one or more desired physico-chemical properties; and perform a virtual screening of the reduced set of target-specific molecules against the target protein to obtain a screened set of target-specific molecules, wherein the screened set of target-specific molecules serve as one or more potential inhibitors of the target protein.

In an embodiment, the target protein specific dataset (TPSD) is a curated target protein specific dataset (CTPSD) obtained by: obtaining a plurality of other proteins having one or more properties similar to one or more corresponding properties of the target protein; and curating a plurality of small molecules comprised in each of the plurality of other proteins to the target protein specific dataset (TPSD).

In an embodiment, the one or more properties similar to the one or more corresponding properties of the target protein comprise at least one of one or more sequence similarities, and a structural similarity (e.g., an active site conservation).

In an embodiment, the CTPSD comprises at least a subset of the plurality of other proteins, and wherein each protein from the subset of the plurality of other proteins comprises one or more small molecules.

In an embodiment, the one or more small molecules are associated with a docking score that is greater than or equal to a threshold score. In one embodiment, the docking score is computed using one or more methods.

In an embodiment, the one or more physico-chemical properties comprise at least one of a Synthetic Accessibility Score (SAS), a biological activity, a partition co-efficient (log P), a molecular weight, and a docking score.

In an embodiment, the set of target-specific small molecules is obtained based on a reward assigned to the target-specific generative model by the RL technique. In one embodiment, a binding affinity of the set of target-specific small molecules is increased based on the reward assigned to the target-specific generative model by the RL technique.

In yet another aspect, there is provided a non-transitory computer readable medium on which a computer readable program is stored, wherein the computer readable program, when executed on a computing device causes the computing device to perform a processor implemented method for predicting potential inhibitors of a target protein comprising receiving an input comprising the target protein; applying a transfer learning technique on a pre-trained generative model using a target protein specific dataset (TPSD) to obtain a target-specific generative model (TSGM) for the target protein; iteratively applying a reinforcement learning (RL) technique on the target-specific generative model and a predictive model to obtain a set of target-specific small molecules, wherein each target-specific small molecule from the set of target-specific small molecules comprises one or more associated physico-chemical properties, wherein the predictive model is pre-trained using a protein dataset, and wherein the one or more associated physico-chemical properties for each target-specific small molecule from the set of target-specific small molecules are predicted by the predictive model; applying one or more filters on each target-specific small molecule from the set of target-specific small molecules to obtain a reduced set of target-specific molecules, wherein each target-specific molecule from the reduced set of target-specific molecules comprises one or more desired physico-chemical properties; and performing a virtual screening of the reduced set of target-specific molecules against the target protein to obtain a screened set of target-specific molecules, wherein the screened set of target-specific molecules serve as one or more potential inhibitors of the target protein.

In an embodiment, the target protein specific dataset (TPSD) is a curated target protein specific dataset (CTPSD) obtained by: obtaining a plurality of other proteins having one or more properties similar to one or more corresponding properties of the target protein; and curating a plurality of small molecules comprised in each of the plurality of other proteins to the target protein specific dataset (TPSD).

In an embodiment, the one or more properties similar to the one or more corresponding properties of the target protein comprise at least one of one or more sequence similarities, and a structural similarity (e.g., an active site conservation).

In an embodiment, the CTPSD comprises at least a subset of the plurality of other proteins, and wherein each protein from the subset of the plurality of other proteins comprises one or more small molecules.

In an embodiment, the one or more small molecules are associated with a docking score that is greater than or equal to a threshold score. In one embodiment, the docking score is computed using one or more methods.

In an embodiment, the one or more physico-chemical properties comprise at least one of a Synthetic Accessibility Score (SAS), a biological activity, a partition co-efficient (log P), a molecular weight, and a docking score.

In an embodiment, the set of target-specific small molecules is obtained based on a reward assigned to the target-specific generative model by the RL technique. In one embodiment, a binding affinity of the set of target-specific small molecules is increased based on the reward assigned to the target-specific generative model by the RL technique.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
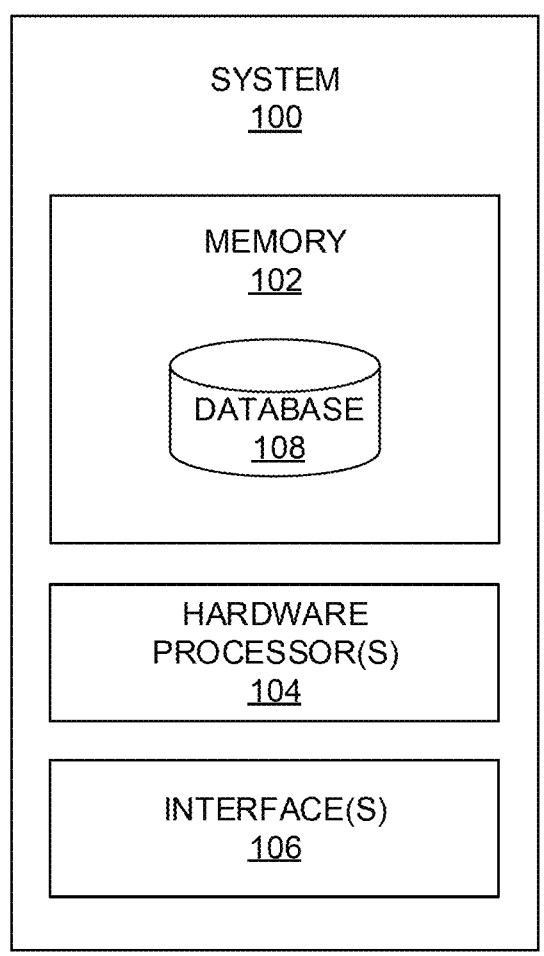
FIG. 1 depicts a system for predicting potential inhibitors of a target protein, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

In a world plagued by the emergence of new diseases, it is essential that the drug design process needs to be accelerated to develop new therapeutics against them. In recent years, deep learning-based methods have shown some success in ligand-based drug design. Yet, these methods face the problem of data scarcity while designing drugs against a novel target. In the present disclosure, embodiments provide systems and methods that leverage the potential of deep learning and molecular modeling approaches to develop a drug design pipeline, which can be useful for cases where there is limited or no availability of target-specific ligand datasets. Inhibitors of other proteins, property wise (or structurally) similar to the target protein are screened at the active site of the target protein to create an initial target-specific dataset. Transfer learning has been implemented by the systems and methods of the present disclosure to learn the features of the target-specific dataset and design new chemical entities using a deep generative model. A deep predictive model has been implemented by the systems and methods of the present disclosure to predict the docking scores of newly designed molecules. Both these models are then combined using reinforcement learning to design new chemical entities with optimized docking score. In the present disclosure, experiment was conducted for the pipeline/method wherein the method has been validated by designing inhibitors against the human JAK2 protein, where none of the existing JAK2 inhibitors were used for training. The ability of the method of the present disclosure to reproduce existing molecules from the validation dataset and design molecules with better binding energy demonstrates its usefulness in designing drugs against any target of emerging disease(s).

Referring now to the drawings, and more particularly to FIGS. 1 through 5D, where similar reference characters denote corresponding features consistently throughout the figures, there are shown preferred embodiments and these embodiments are described in the context of the following exemplary system and/or method.

FIG. 1 depicts a system 100 for predicting potential inhibitors of a target protein, in accordance with an embodiment of the present disclosure. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is/are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises drug-like molecules in a pre-defined format (e.g., Simplified Molecular Input Line Entry System (SMILES) format). The database 108 further stores other inputs such as information on target protein for which potential inhibitors are predicted. Other information comprised in the database 108 comprises small molecules comprised in each of the plurality of other proteins for curation and obtaining a curated target protein specific dataset (CTPSD) thereof. The database 108 further stores various techniques such as transfer learning technique(s), reinforcement learning technique(s), target-specific generative model(s), predictive model(s), and the like. The above-mentioned techniques and the models comprised in the memory 102/database 108 are invoked as per the requirement by the system 100 to perform the methodologies described herein. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figure 2:
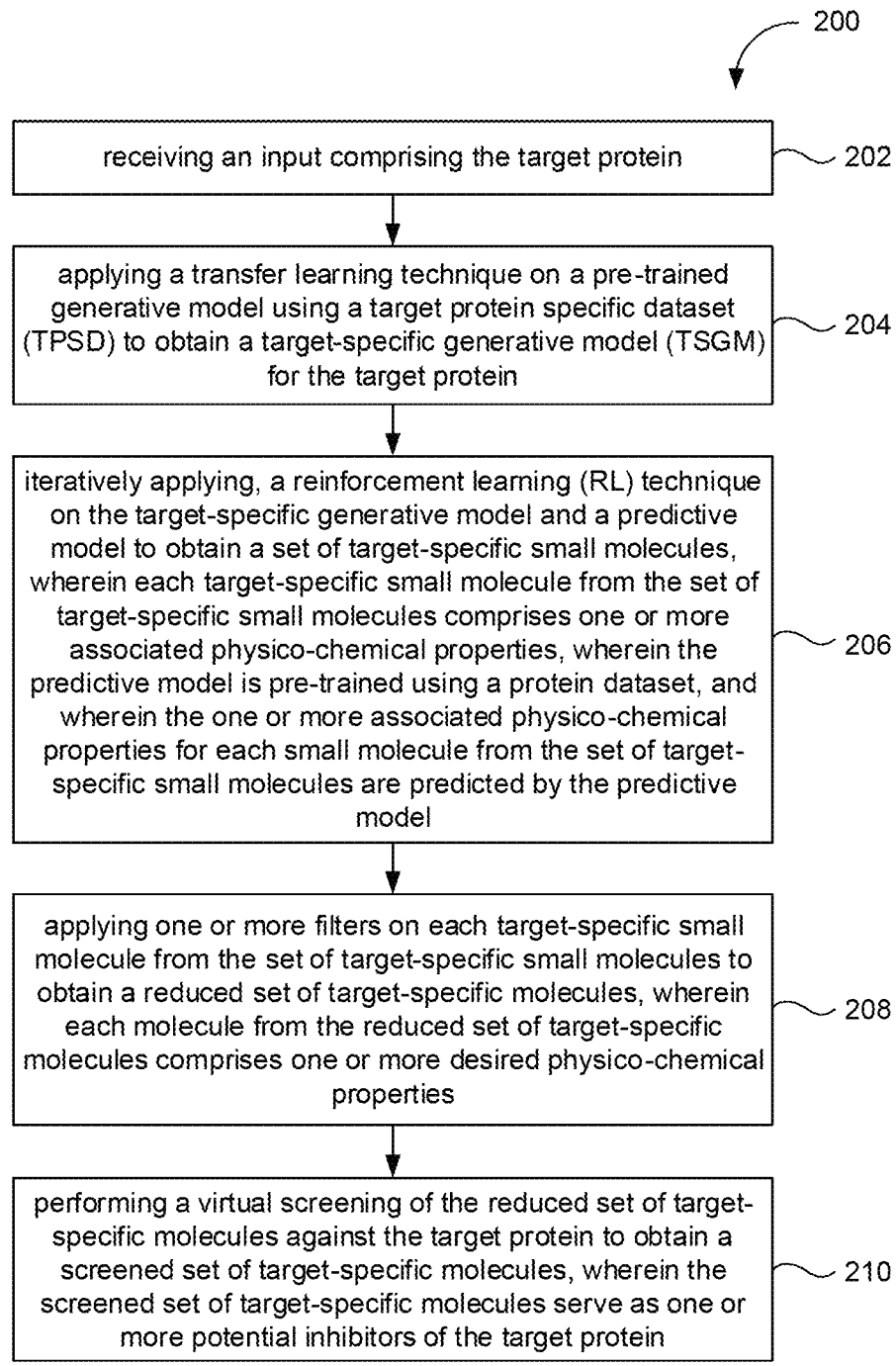
FIG. 2 depicts an exemplary flow chart illustrating a processor implemented method for predicting potential inhibitors of a target protein, using the system of FIG. 1, in accordance with an embodiment of the present disclosure.

FIG. 2, with reference to FIG. 1, depicts an exemplary flow chart illustrating a processor implemented method 200 for predicting potential inhibitors of a target protein, using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, and the flow diagram as depicted in FIG. 2. In an embodiment, at step 202 of the present disclosure, the one or more hardware processors 104 receive an input comprising a target protein. In the present disclosure, the target protein described is human Janus kinase 2 (JAK2). It is a tyrosine kinase protein known for its major role in JAK/STAT signaling pathway. It is also involved in various essential cellular processes including cell growth, development, differentiation, and histone modifications. It regulates both innate and adaptive immune systems and dysfunction of JAK2 has been implicated in multiple conditions such as myelofibrosis and thrombocythemia. Given the availability of considerable experimental results, JAK2 serves as a good example of a target protein to validate the proposed method/system. It is to be understood by a person having ordinary skill in the art or person skilled in the art that such example of target protein JAK2 shall not be construed as limiting the scope of the present disclosure.

At step 204 of the present disclosure, the one or more hardware processors 104 apply a transfer learning technique on a pre-trained generative model using a target protein specific dataset (TPSD) to obtain a target-specific generative model (TSGM) for the target protein. Example of TPSD is shown below and such examples of TPSD shall not be construed as limiting the scope of the present disclosure.

ChEMBL_385598

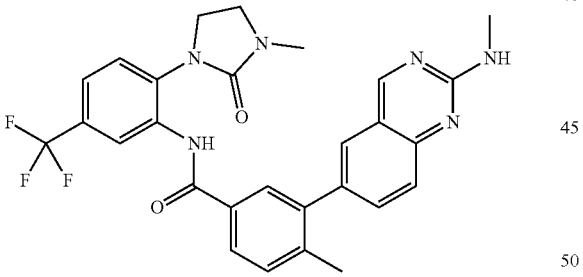

ChEMBL_1879463

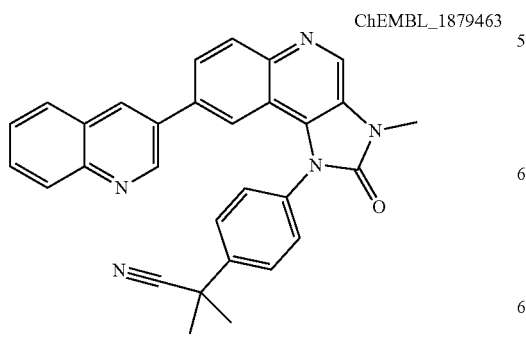

-continued

ChEMBL_4076473

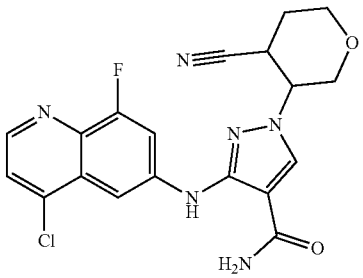

Example of small molecules generated by the TSGM is shown below and such examples of small molecules generated by the TSGM shall not be construed as limiting the scope of the present disclosure.

Mol_1491

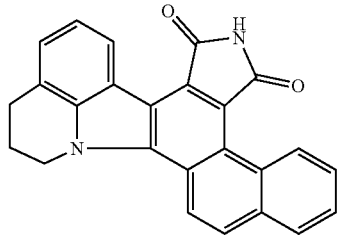

Mol_2291

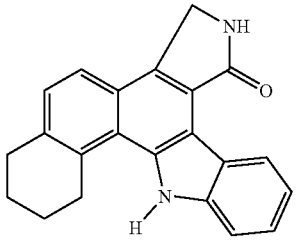

Mol_2673

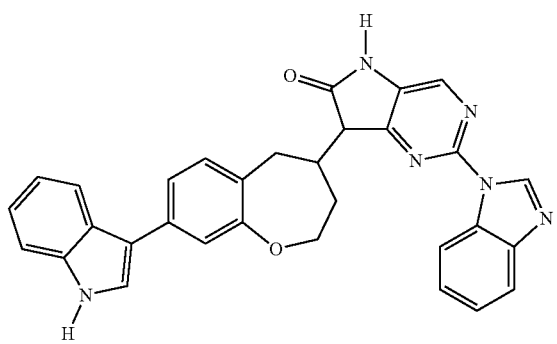

-continued

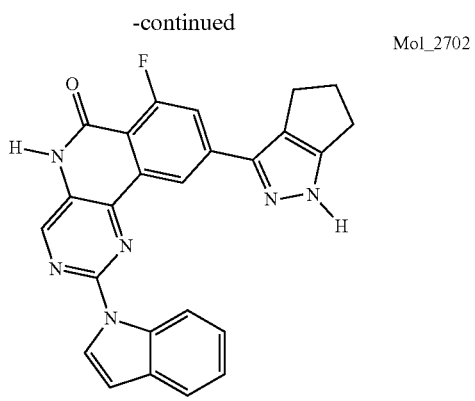

Mol_2702

In an embodiment of the present disclosure the pre-trained generative model is obtained by: obtaining an input dataset comprising drug-like molecules in a pre-defined format (e.g., SMILES format) and training a generative model (e.g., a recurrent neural network (RNN)) with the received input dataset to obtain the pre-trained generative model. It is to be understood by a person having ordinary skill in the art or person skilled in the art that the example of RNN shall not be construed as limiting the scope of present disclosure for arriving at the pre-trained generative model as an output upon applying the TL technique. Dataset for training the generative model and for the case study were obtained from the ChEMBL database. Molecules were represented in the SMILES format to leverage the effectiveness of recurrent neural networks (RNNs) in handling sequential data through existing natural language processing algorithms. RDKit library in Python was used for dataset pre-processing. In an embodiment, the target protein specific dataset (TPSD) is a curated target protein specific dataset (CTPSD) which is generated by obtaining a plurality of other proteins having one or more properties similar to one or more corresponding properties of the target protein and curating a plurality of small molecules comprised in each of the plurality of other proteins. The one or more properties similar to the one or more corresponding properties of the target protein comprise at least one of one or more sequence similarities, and a structural similarity. The CTPSD comprises at least a subset of the plurality of other proteins, and wherein each protein from the subset of the plurality of other proteins comprises one or more small molecules, in one example embodiment of the present disclosure (e.g., refer FIG. 3). The one or more small molecules are associated with a docking score that is greater than or equal to a threshold score. In an embodiment of the present disclosure the threshold score may be one of a pre-defined score or an empirically determined score. The docking score is computed using one or more methods as known in the art.

In other words, the curation results in the TPSD serves as an input for TL technique at step 204. A set of 2D molecular structures of small molecules from the TPSD curated for the case study being discussed in the present disclosure is shown above. The above step of obtaining other proteins and curating molecules associated thereof can be better understood by way of following example: The pre-trained generative model which has learnt the SMILES grammar was subject to transfer learning, in order to design small molecules specific to the target protein of interest. Transfer learning requires a ligand dataset specific to the target protein of interest, to delineate the target-specific features to the generative model. Systems and methods of the present disclosure assumed that there is no prior knowledge about the inhibitors of JAK2. With the above assumption, a set of inhibitors of proteins, which are property wise (or structurally) similar to the JAK2 protein were identified. To identify the human proteins with high active site similarity to the JAK2 protein, a sequence similarity search was performed with the sequence of the JAK2 protein (UniProt ID: O60674) against all human proteins (using BLASTp). From the search results it was observed that, the kinase domains of three other human proteins namely, JAK1, JAK3 and TYK2 possess high sequence similarity with the kinase domain of JAK2. The above explanation can be better understood by the following description.

As mentioned above, the human Janus kinase (JAK) family of proteins play a very essential role in the innate and adaptive immune systems, by interacting with cytokines through the JAK/STAT signaling pathway. Multiple mutations in the four proteins of the JAK family namely, JAK1, JAK2, JAK3 and TYK2, have been implicated in various immune disorders and cancers.

The multiple sequence alignment (MSA) of the sequence of the kinase domains of the four JAK family proteins can be obtained (using the Clustal Omega (v1.2.4) program as known in the art). The protein sequences were collected from UniProt (JAK1-P23458, JAK2-O60674, JAK3-P52333, TYK2-P29597). The sequence in italic font indicates the start of the kinase domain of the three proteins based on the crystal structures from Protein Data Bank (JAK1-PDB ID: 6N7A, JAK2-PDB ID: 4IVA, JAK3-PDB ID: 5LWM, TYK2-PDB ID: 4GFO). The region of the sequence with text underlined indicates the sequentially discontinuous active site of the protein. Although the structures of the four kinase domains could be aligned with <1.1 Å RMSD (refer FIG. 3), the sequence of the active site indicates the residue-level variations between the three proteins. More specifically, FIG. 3, with reference to FIGS. 1 and 2, depicts alignment of crystallographic structures of the kinase domains of the proteins from Janus kinase family—JAK1 (PDB ID: 6N7A), JAK2 (PDB ID: 4IVA), JAK3 (PDB ID: 5LWM) and TYK2 (PDB ID: 4GFO), in accordance with an embodiment of the present disclosure.

Although the overall fold of all the four proteins is highly conserved, there are minor changes in the active site. Such changes in the active site can alter the binding mode of the ligands, thereby influencing the biological effect of the ligand on the target protein. For instance, experimental studies indicate that, the presence of a cysteine instead of a serine in the active site (residue 909) of JAK3, enables selectivity of the ligands through covalent interactions.

Although the elements of the active site responsible for ligand selectivity have been delineated for JAK3, the selectivity of ligands and cytokines towards the other JAK family proteins still remains unclear. The major role of JAK/STAT pathway in the regulation of immune response and the non-redundant role of the JAK family proteins in the activation of the pathway, highlight the need to understand the selective mechanism of activation of JAK family proteins through designing selective inhibitors against them. Despite observed sequence variations among the active site residues, a comparison of the active sites of the four proteins of the human Janus kinase protein family reveals that, the kinase domains have a conserved active site structure (e.g., refer FIG. 3), which can be leveraged to enumerate the molecular features required for selective design of inhibitors against the proteins.

Motivated by the structural similarity of the active sites, the ligands known to inhibit JAK1, JAK3 and TYK2 proteins were chosen to construct the target-specific training dataset. An the datasets with their experimentally determined IC50 values were collected from the ChEMBL database. The IC50 values were converted to log scale to obtain the pChEMBL score. After pre-processing, canonicalization, removal of redundant molecules and filtration, a dataset of 3,711 inhibitors were curated. A validation dataset of 1,103 unique JAK2 inhibitors from ChEMBL database was also curated.

To ensure the specificity of the 3,711 inhibitors, the dataset was screened at the active site of human JAK2 protein using docking (AutoDock Vinay. Only 3,681 molecules with virtual screening score<=−7.0 were utilized for training the generative model using TL technique. In other words, in case of the JAK2 protein, the other proteins with highly conserved active site and similar biological function were identified to be—JAK1, JAK3 and TYK2. The process of CTPSD curation is detailed below.
1. For a target protein with low or no data on small molecules which can bind to it, a sequence similarity search is performed using the Basic Local Alignment Search Tool (BLASTp) with all the other proteins (preferably from the same organism). The protein sequences which exhibit high query coverage, low e-value and high percent identity with the target protein sequence are chosen. These are the proteins considered to be similar to the target protein of interest initially.
2. The experimentally determined three-dimensional structure of the target protein and the similar proteins (from BLASTp search) are collected. The active site of all the similar proteins, the overall fold of the proteins and the primary biological function performed by the proteins are compared with the target protein. The proteins which are found to have high active site similarity, similar fold and function compared to the target protein are chosen for curating the target-specific training dataset.
3. AH the small molecules known to inhibit the proteins similar to the target protein are collected, pre-processed and duplicates are removed.
4. These small molecules are screened/docked at the active site of the target protein of interest to understand their specificity towards the target protein. Only molecules with high virtual screening scores (<=−7.0) are chosen to form the final target-specific small molecule dataset for transfer learning.

Referring to steps of FIG. 2, at step 206 of the present disclosure, the one or more hardware processors 104 iteratively apply a reinforcement learning (RL) technique on (i) the target-specific generative model and (ii) a predictive model to obtain a set of target-specific small molecules. Each target-specific small molecule from the set of target-specific small molecules comprises one or more associated physico-chemical properties. The one or more associated physico-chemical properties comprise at least one of a Synthetic Accessibility Score (SAS), a biological activity, a partition co-efficient (log P), a molecular weight, and a docking score, in one embodiment of the present disclosure.

Figure 3:
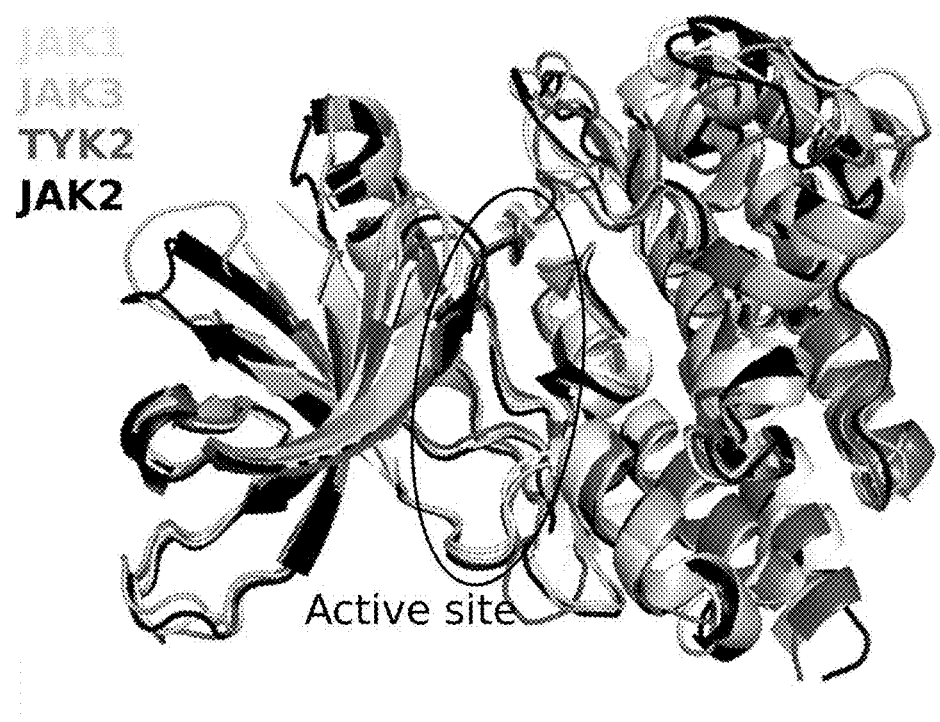
FIG. 3 depicts alignment of crystallographic structures of the kinase domains of the proteins from Janus kinase family—JAK1 (PDB ID: 6N7A), JAK2 (PDB ID: 4IVA), JAK3 (PDB ID: 5LWM) and TYK2 (PDB ID: 4GFO), in accordance with an embodiment of the present disclosure.

In the present disclosure, the set of target-specific small molecules is obtained based on a reward assigned to the target-specific generative model by the RL technique. A binding affinity of the set of target-specific small molecules is increased based on the reward assigned to the target-specific generative model by the RL technique, in one embodiment of the present disclosure. FIGS. 4A through 4G, with reference to FIGS. 1 through 3, depict a graphical representation illustrating optimization of the distribution of docking score with the progress in reinforcement learning (RL) technique, in accordance with an embodiment of the present disclosure. The graphical representations have been provided for once in every 10 epochs of RL training until the 70th epoch when the RL training process was concluded.

In the present disclosure, the predictive model is pre-trained using a protein dataset wherein the one or more associated physico-chemical properties for each target-specific small molecule from the set of target-specific small molecules are predicted by the predictive model. In the present disclosure, the generative model was trained on a dataset of ~1.6 million SMILES strings from the ChEMBL database. The use of stack-augmented memory enabled the generation of chemically valid SMILES with high accuracy. More specifically, the predictive model was trained to predict the docking score of the generated small molecules. The dataset of 4,167 molecules with their docking scores against the JAK2 protein was used to train the predictive model.

The predictive model learns a mapping between the small molecules (represented as SMILES strings) and their corresponding docking scores (using AutoDock Vina as known in the art). The model was trained using mini-batch gradient descent with the Adam optimizer. After extensive hyperparameter tuning, the predictive model could predict the docking score for any given SMILES string, within a root mean square error (RMSE) of 0.5 (a comparison between the predicted and observed docking scores was performed which explains the effectiveness of the predictive model).

The above step of iteratively performing RL technique may be better understood by way of the following description and explanation:

The target-specific generative model (TSGM) obtained after TL, was considered as the agent. Docking score predictive model was considered as the critic. For optimization of the docking score, the following reward function was used:

$$r(x) = \exp\left(\frac{-x}{3.0}\right)$$

where, x is the docking score from the predictive model and r(x) is the reward for reinforcing/penalizing the target-specific generative model. For every epoch of RL training phase, 50 molecules were sampled from the target-specific generative model and their reward was calculated with the above reward function. The reward was used to optimize the target-specific generative model iteratively using a regularized loss function. Below Table 1 illustrates examples of target-specific small molecules from the target-specific generative model after RL and their physico-chemical properties.

TABLE 1

| Molecule ID | logP* | MW* (Da) | HBA* | HBD* | NRB* | TPSA* (Å$^2$) | Benzene count | SAS* | Docking score |
|---|---|---|---|---|---|---|---|---|---|
| Mol_1491 | 4.93 | 376 | 3 | 1 | 0 | 51.1 | 5 | 2.65 | −12.6 |
| Mol_2291 | 4.59 | 326 | 1 | 2 | 0 | 44.89 | 4 | 3.49 | −12.5 |
| Mol_2673 | 5.17 | 513 | 7 | 2 | 3 | 106.41 | 7 | 3.38 | −11.9 |
| Mol_2702 | 4.43 | 436 | 5 | 2 | 2 | 92.25 | 6 | 3.06 | −12.4 |

*log P—Partition coefficient; MW—Molecular Weight; HBA—Hydrogen Bond Acceptor; HBD—Hydrogen Bond Donor; TPSA—Topological Polar Surface Area; SAS—Synthetic Accessibility Score.

At step 208 of the present disclosure, the one or more hardware processors 104 apply one or more filters on each target-specific small molecule from the set of target-specific small molecules to obtain a reduced set of target-specific molecules. Each target-specific small molecule from the reduced set of target-specific small molecules comprises one or more desired physico-chemical properties.

For the JAK2 case study, the following values were used for various physico-chemical property filters.
1. 200 Da<MW<700 Da
2. log P<6.0
3. SAS<5.0

The above property filters are helpful to decide whether the molecules possess desired drug-like properties.

FIGS. 5A through 5D, with reference to FIGS. 1 through 4G, depict a graphical representation illustrating distribution of physico-chemical properties for all the target-specific small molecules from the TSGM obtained after reinforcement learning (RL) technique being performed at step 206, in comparison with that of the curated TPSD, in accordance with an embodiment of the present disclosure. As can be seen from the graphical representations depicted in FIGS. 5A through 5D, the molecular weight, log P and QED of the designed small molecules are closely similar to the curated target protein-specific dataset (which are also drug-like molecules) while, the synthetic accessibility score (SAS) has shown an improvement after RL technique being performed (the lower the SAS value, the better).

Figure 4A:
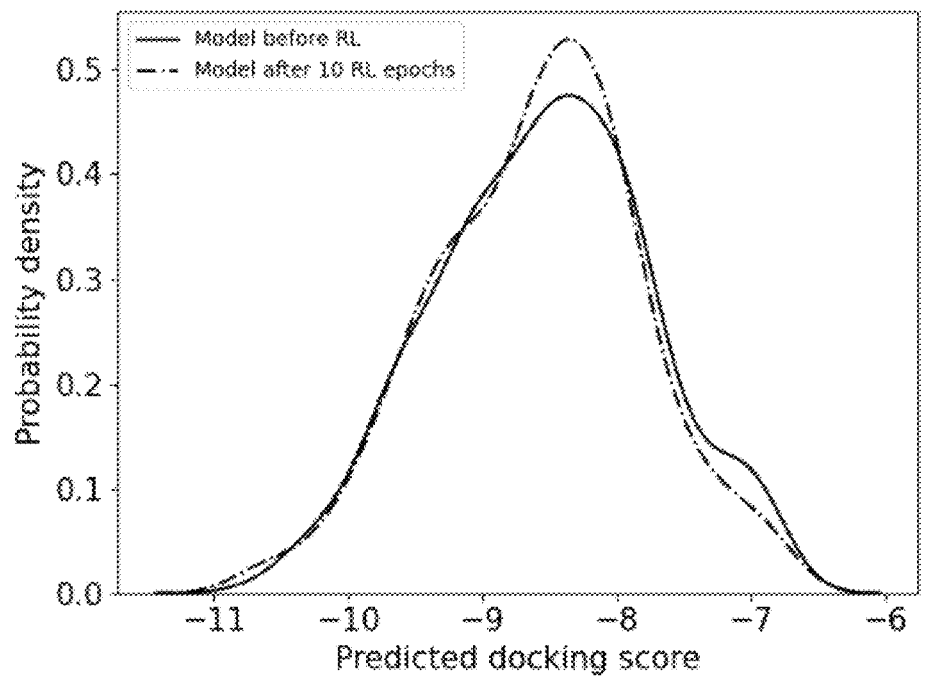
FIGS. 4A through 4G depict a graphical representation illustrating optimization of the distribution of docking score with the progress in reinforcement learning (RL) technique, in accordance with an embodiment of the present disclosure.
Figure 4B:
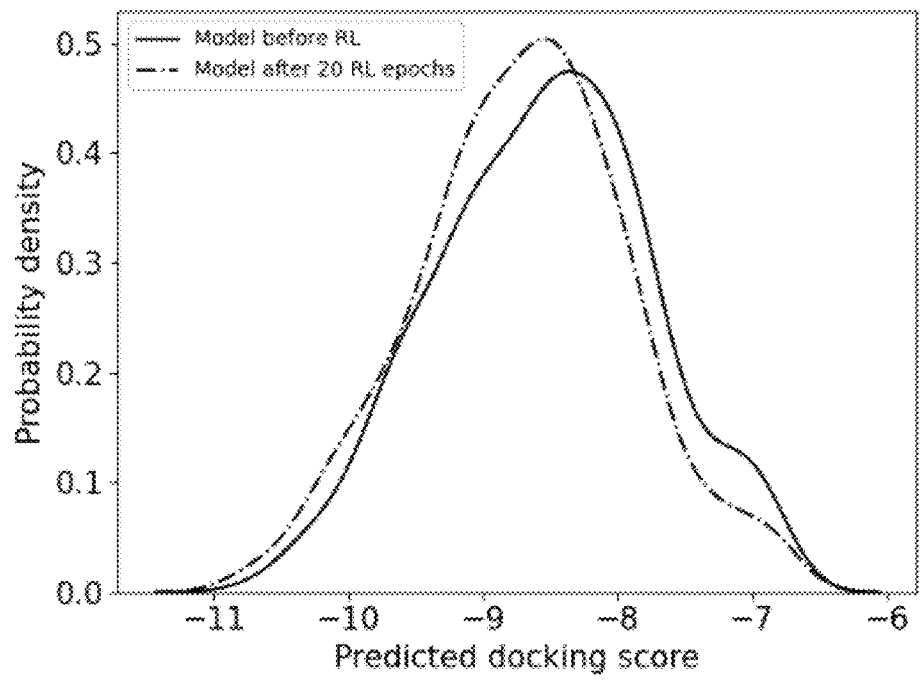
Figure 4C:
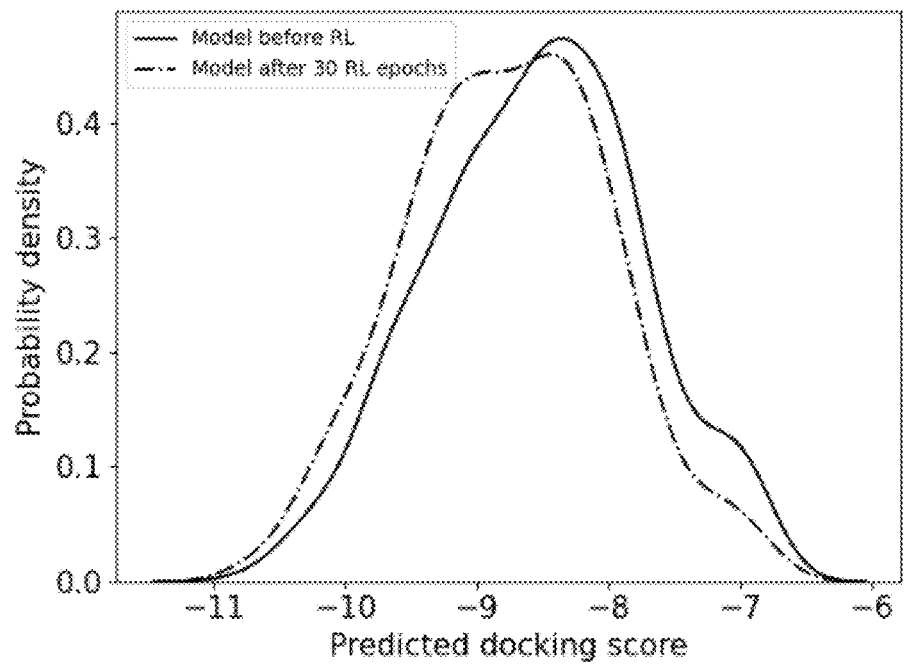
Figure 4D:
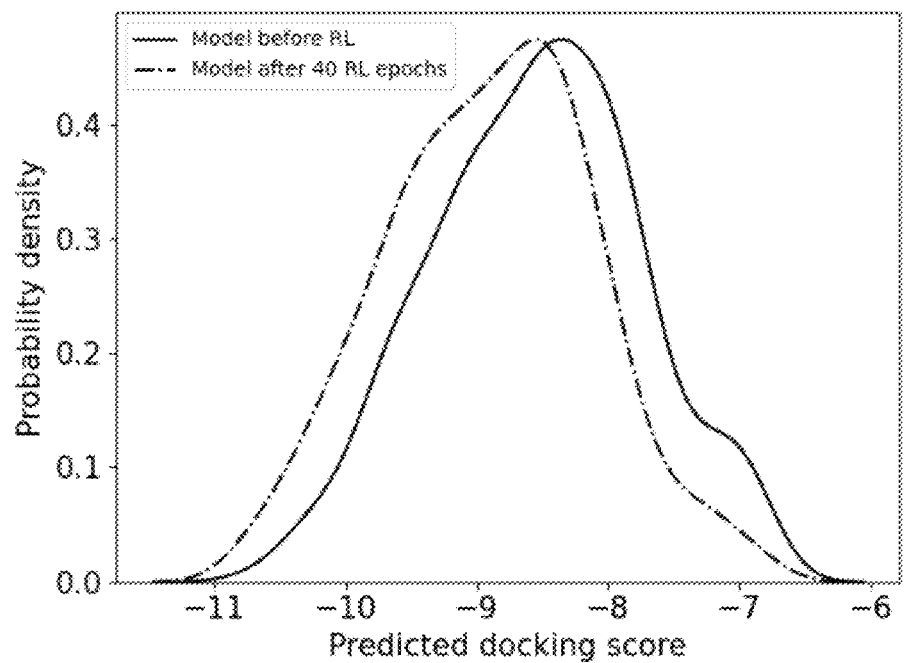
Figure 4E:
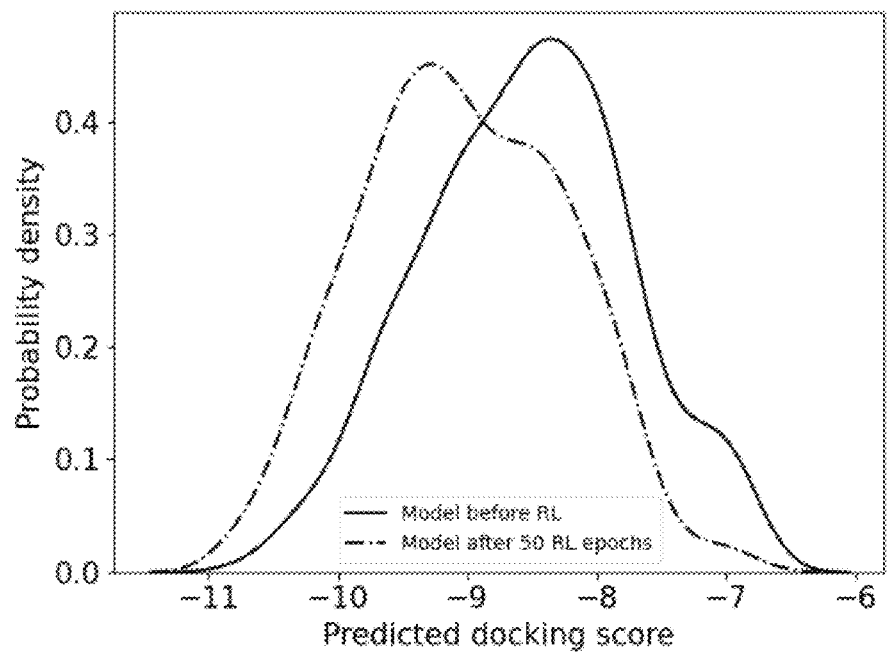
Figure 4F:
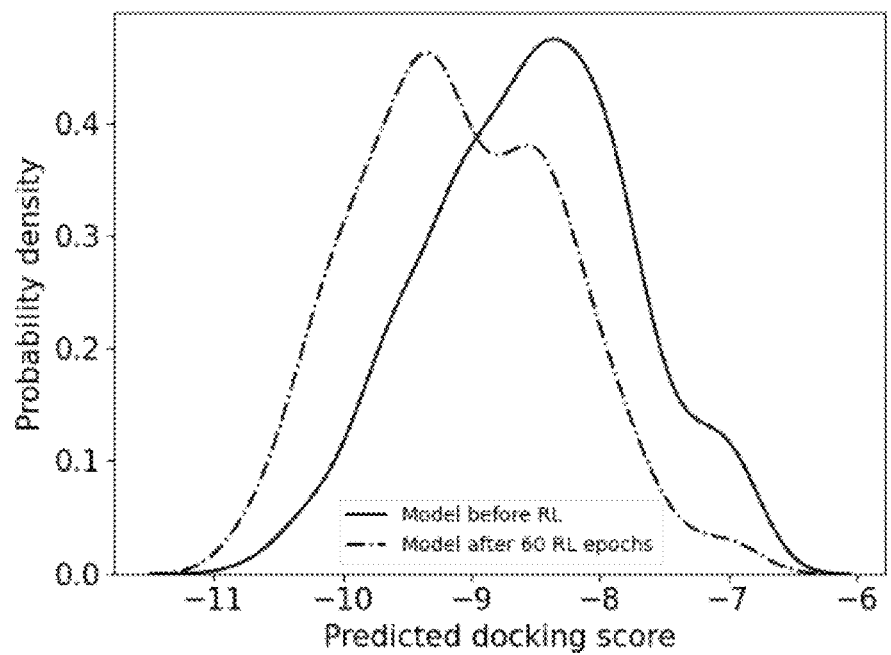
Figure 4G:
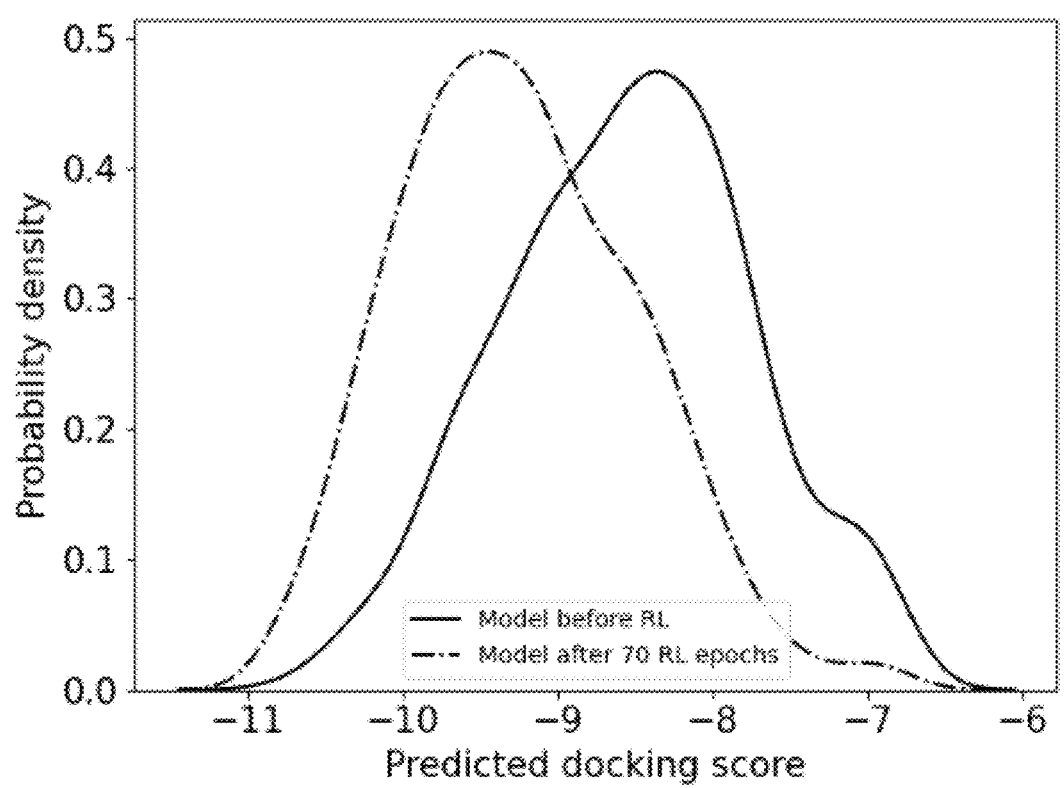
Figure 5A:
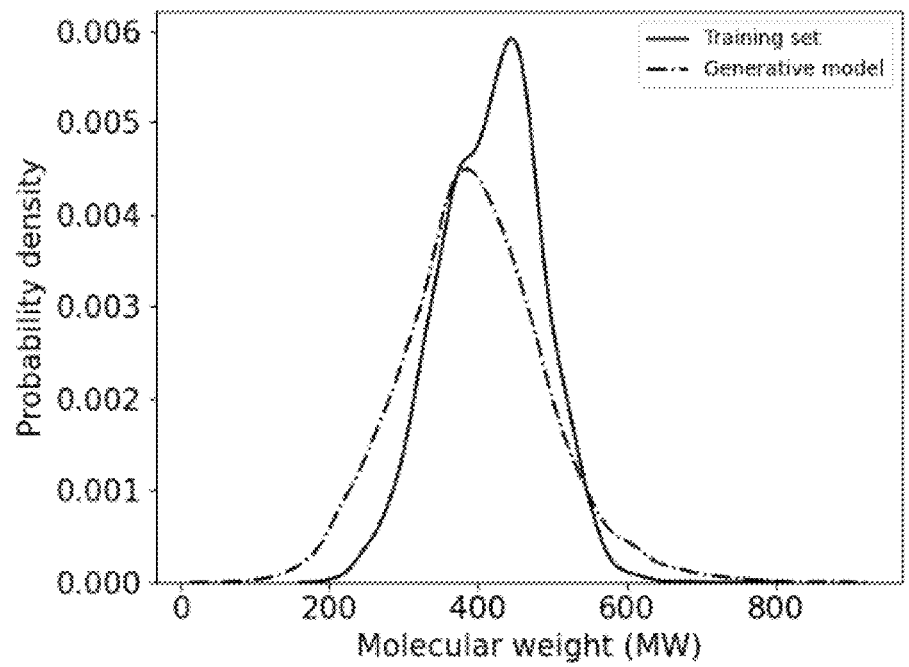
FIGS. 5A through 5D depict a graphical representation illustrating distribution of physico-chemical properties for all the target-specific small molecules from the TSGM obtained after reinforcement learning (RL) technique being performed in method steps of FIG. 2, in comparison with that of the curated TPSD, in accordance with an embodiment of the present disclosure.
Figure 5B:
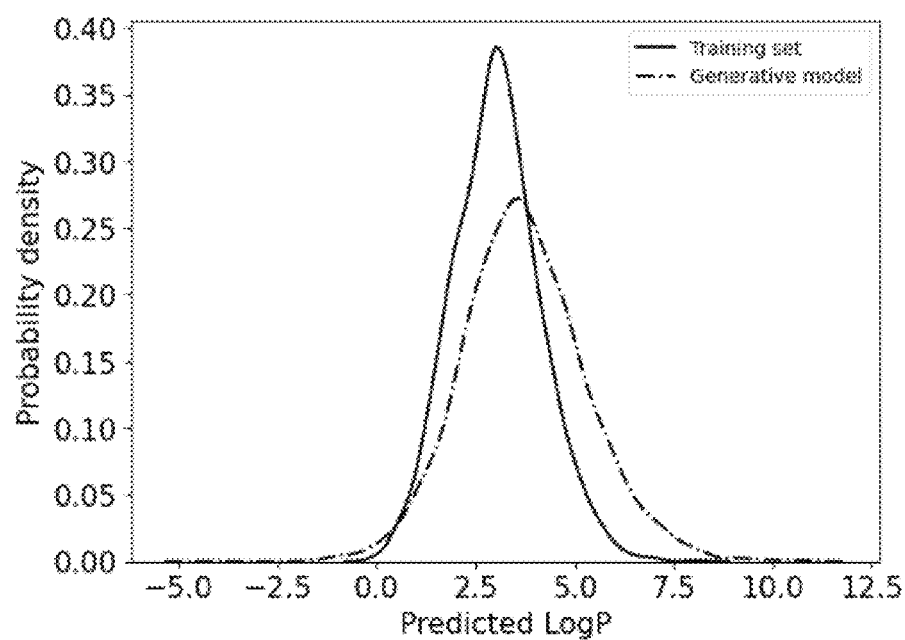
Figure 5C:
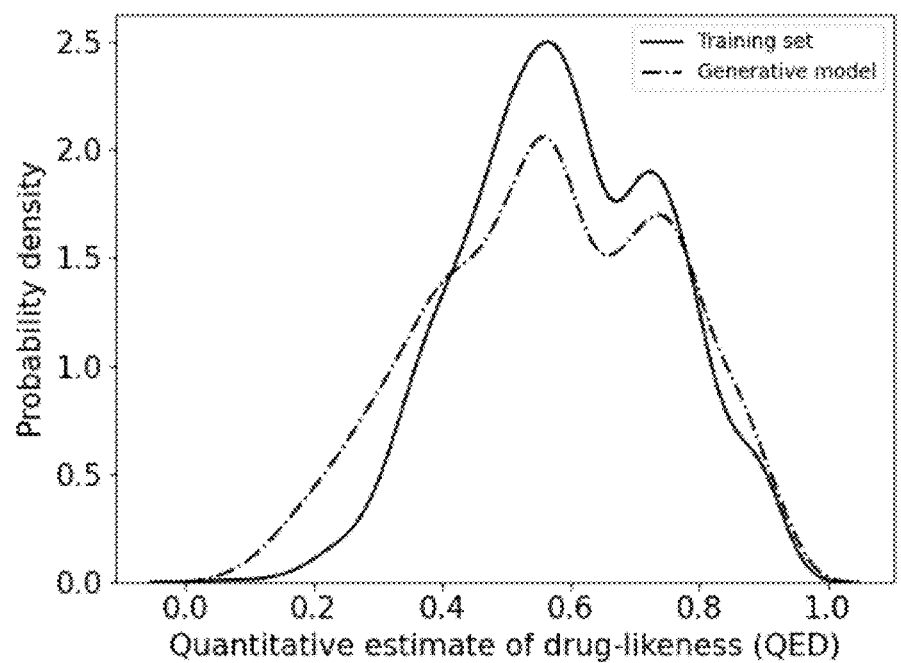
Figure 5D:
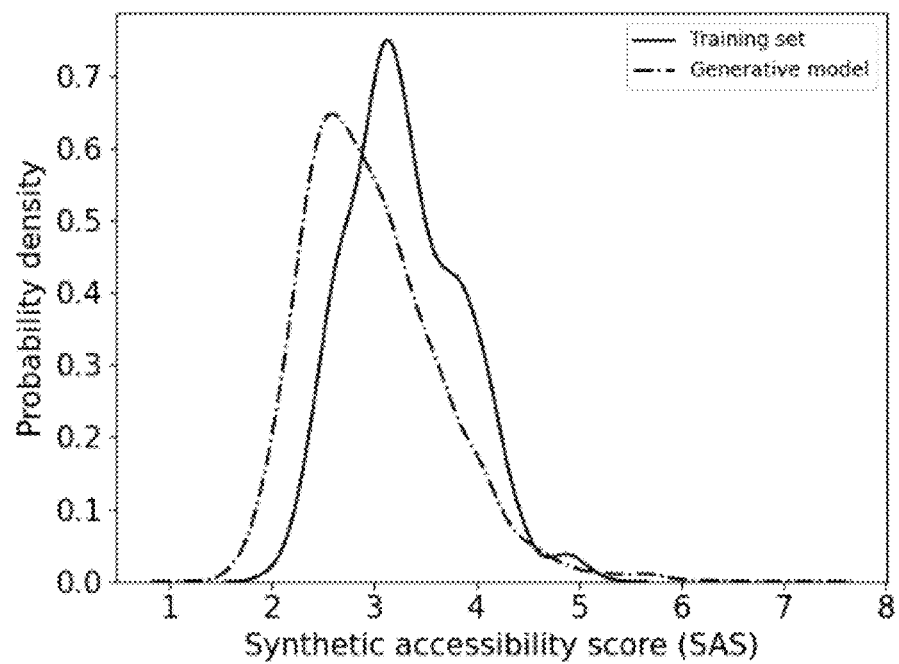

The target-specific generative model obtained after TL was further subjected to docking score optimization with the predictive model using regularized reinforcement learning (RL) for 70 epochs. The distribution of predicted docking scores before and after RL was considered as the criterion for terminating the training process (FIG. 4B). After RL, 10,000 molecules were sampled from the trained generative model. 93% (9,290) of the generated small molecules were found to be chemically valid, indicating the robustness of the model against catastrophic "forgetting". Upon removal of redundant (15.76%) and training set-identical molecules (2.45%), 7,469 small molecules were obtained.

Next, various drug-like physico-chemical property filters were applied to obtain molecules with drug-like properties. These included, octanol-water partition coefficient (log P), molecular weight (MW) and the synthetic accessibility score (SAS). SAS was used as a filter to avoid molecules which are difficult to synthesize. With the application of property filters (200 Da<MW<700 Da, log P<6.0 and SAS<5.0), a dataset of 6,691 molecules was obtained. Finally, 6,106 small molecules with docking score<=−7.0 were considered for further analysis.

Upon obtaining the reduced set of target-specific molecules, at step 210 of the present disclosure, the one or more hardware processors 104 perform a virtual screening of the reduced set of target-specific molecules against the target protein to obtain a screened set of target-specific molecules. The screened set of target-specific molecules serve as one or more potential inhibitors of the target protein, in one embodiment of the present disclosure. The molecules provided above as examples from the TSGM are also examples of the molecules obtained after virtual screening against the JAK2 protein. The virtual screening was performed using the open-source docking software—(AutoDock Vina as known in the art), in one embodiment of the present disclosure. A grid box was set at the active site of the JAK2 protein, to define the search space for the screening process. Within the grid box, each of the small molecules designed by the TSGM was screened and the docking score from the screening was used as a measure of binding affinity to filter the small molecules. The procedure is widely used to screen the small molecules. After virtual screening, the small molecules were further compared to the dataset of 1,103 JAK2-specific small molecules set aside for validation. It was observed that, 5% of the JAK2-specific small molecules generated by the target-specific generative model were highly similar to the small molecules from the validation dataset (quantified by >=0.75 Tanimoto coefficient). This indicates the ability of the target-specific generative model to generate highly selective and diverse small molecules with similarity to the existing target protein-specific small molecules.

Embodiments of the present disclosure provide systems and methods for predicting potential inhibitors of target proteins. More specifically, the present disclosure provides systems and methods for generating small molecules against any target of interest. The method is particularly applicable for cases where no target-specific small molecule dataset is available. The method overcomes the problem of data availability for novel target proteins of interest, by utilizing inhibitors of proteins with similar active site in order to curate a target protein specific dataset, which can be used to train the deep neural network models. By addressing the data availability issue for novel target proteins, the method is also amenable to be used to design novel small molecules against conserved proteins of novel pathogens. From the case study it can be inferred that, transfer learning and reinforcement learning enables the model to generate molecules similar to the validation dataset, while also being able to optimize the affinity of the molecules towards the target protein of interest. The ability of the target-specific generative model to generate small molecules with improved virtual screening scores, showcases the effectiveness of RL in optimizing the generative model. Analysis of the sub-structural fragments present among the generated small molecules also indicates that, the molecules are selective against the JAK2 active site and are easy to synthesize. While the method was validated by its ability to reproduce molecules from the validation dataset, several molecules with better binding capability (quantified by their docking score) were also observed.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for predicting potential inhibitors of a target protein, the method comprising:
receiving, via one or more hardware processors, an input comprising the target protein;
applying, via the one or more hardware processors, a transfer learning technique on a pre-trained generative model using a target protein specific dataset (TPSD) to obtain a target-specific generative model (TSGM) for the target protein and learn target-specific features of the target protein specific dataset and design new chemical molecules, wherein the pre-trained generative model is obtained by: obtaining an input dataset comprising molecules in a pre-defined format and training a generative model with the input dataset to obtain the pre-trained generative model, and the target protein specific dataset (TPSD) is a curated target protein specific dataset (CTPSD) obtained by:
obtaining a plurality of other proteins having one or more properties similar to one or more corresponding properties of the target protein; and
iteratively applying, via the one or more hardware processors, a reinforcement learning (RL) technique on the target-specific generative model and a predictive model to obtain a set of target-specific small molecules, wherein each target-specific small molecule from the set of target-specific small molecules comprises one or more associated physico-chemical properties and the one or more associated physico-chemical properties comprise a Synthetic Accessibility Score (SAS), a biological activity, a partition co-efficient (log P), a molecular weight, and the docking score, and the predictive model is pre-trained using a protein dataset, wherein the predictive model predicts the one or more associated physico-chemical properties for each target-specific small molecule from the set of target-specific small molecules, and the RL technique (i) obtains the set of target-specific small molecules based on a reward assigned to the target-specific generative model and (ii) increases binding affinity of the set of target-specific small molecules based on the reward assigned to the target-specific generative model, wherein the reward is used to optimize the target-specific generative model iteratively using a regularized reward function, and the target-specific generative model is subjected to the docking score optimization with the predictive model using a regularized reinforcement learning (RL) technique, and wherein the regularized reward function comprises:

$$r(x) = \exp\left(\frac{-x}{3.0}\right)$$

where x is a docking score from the predictive model and r (x) is the reward for reinforcing the target-specific generative model;
applying, via the one or more hardware processors, physico-chemical property filters on each target-specific small molecule from the set of target-specific small molecules to obtain a reduced set of target-specific molecules, wherein the physico-chemical property filters relate to octanol-water partition coefficient (log P), molecular weight (MW) and synthetic accessibility score (SAS) associated with each target-specific small molecule, and the SAS avoids molecules which are difficult to synthesize, and each molecule from the reduced set of target-specific molecules comprises one or more desired physico-chemical properties, and small molecules are docked at an active site of the target protein are chosen to curate a target specific training dataset and molecules with high virtual screening scores (<=−7.0) are chosen to form a final target-specific small molecule dataset for transfer learning;

performing, via the one or more hardware processors, a virtual screening of the reduced set of target-specific molecules against the target protein to obtain a screened set of target-specific molecules, wherein the screened set of target-specific molecules serve as one or more potential inhibitors of the target protein; and validating, via the one or more hardware processors, the screened set of target-specific molecules by comparing the screened set of target-specific molecules with a dataset of target-specific small molecules set aside for validation, wherein selective and diverse small molecules similar to the dataset of the target-specific small molecules are generated using the target-specific generative model by optimizing affinity of the small molecules towards the target protein by utilizing inhibitors of proteins with similar active site, thereby reproducing the existing target-specific small molecules from a validation dataset.

2. The processor-implemented method of claim 1, wherein the CTPSD comprises at least a subset of the plurality of other proteins, and each protein from the subset of the plurality of other proteins comprises one or more small molecules.

3. A system for predicting potential inhibitors of a target protein, comprising:

a memory storing instructions;

one or more communication interfaces; and one or more hardware processors coupled to the memory via the one or more communication interfaces, wherein the one or more hardware processors are configured by the instructions to:

receive an input comprising the target protein;

apply a transfer learning technique on a pre-trained generative model using a target protein specific dataset (TPSD) to obtain a target-specific generative model (TSGM) for the target protein and learn target-specific features of the target protein specific dataset and design new chemical molecules, and the pre-trained generative model is obtained by: obtaining an input dataset comprising molecules in a pre-defined format and training a generative model with the input dataset to obtain the pre-trained generative model, and wherein the target protein specific dataset (TPSD) is a curated target protein specific dataset (CTPSD) obtained by:

obtaining a plurality of other proteins having one or more properties similar to one or more corresponding properties of the target protein; and iteratively apply a reinforcement learning (RL) technique on the target-specific generative model and a predictive model to obtain a set of target-specific small molecules, wherein each target-specific small molecule from the set of target-specific small molecules comprises one or more associated physico-chemical properties and the one or more associated physico-chemical properties comprise a Synthetic Accessibility Score (SAS), a biological activity, a partition co-efficient (log P), a molecular weight, and the docking score, and the predictive model is pre-trained using a protein dataset, and the predictive model predicts the one or more associated physico-chemical properties for each target-specific small molecule from the set of target-specific small molecules, wherein the RL technique (i) obtains the set of target-specific small molecules based on a reward assigned to the target-specific generative model and (ii) increases binding affinity of the set of target-specific small molecules based on the reward assigned to the target-specific generative model, and the reward is used to optimize the target-specific generative model iteratively using a regularized reward function, and the target-specific generative model is subjected to the docking score optimization with the predictive model using a regularized reinforcement learning (RL) technique, and the regularized reward function comprises:

$$r(x) = \exp\left(\frac{-x}{3.0}\right)$$

where x is a docking score from the predictive model and r (x) is the reward for reinforcing the target-specific generative model;

apply physico-chemical property filters on each target-specific small molecule from the set of target-specific small molecules to obtain a reduced set of target-specific molecules, wherein the physico-chemical property filters relate to an octanol-water partition coefficient (log P), a molecular weight (MW) and the synthetic accessibility score (SAS) associated with each target-specific small molecule, and the SAS avoids molecules which are difficult to synthesize, and each molecule from the reduced set of target-specific molecules comprises one or more desired physico-chemical properties, and small molecules are docked at an active site of the target protein are chosen to curate a target specific training dataset and molecules with high virtual screening scores (<=−7.0) are chosen to form a final target-specific small molecule dataset for transfer learning;

perform a virtual screening of the reduced set of target-specific molecules against the target protein to obtain a screened set of target-specific molecules, wherein the screened set of target-specific molecules serve as one or more potential inhibitors of the target protein; and validate the screened set of target-specific molecules by comparing the screened set of target-specific molecules with a dataset of target-specific small molecules set aside for validation, wherein selective and diverse small molecules similar to the dataset of the target-specific small molecules are generated using the target-specific generative model by optimizing affinity of the small molecules towards the target protein by utilizing inhibitors of proteins with similar active site, thereby reproducing the existing target-specific small molecules from a validation dataset.

4. The system of claim 3, wherein the CTPSD comprises at least a subset of the plurality of other proteins, and wherein each protein from the subset of the plurality of other proteins comprises one or more small molecules.

5. A non-transitory computer readable medium on which a computer readable program is stored, wherein the computer readable program, when executed on a computing device causes the computing device to perform a processor-implemented method for predicting potential inhibitors of a target protein comprising:

receiving an input comprising the target protein;

applying a transfer learning technique on a pre-trained generative model using a target protein specific dataset (TPSD) to obtain a target-specific generative model (TSGM) for the target protein and learn target-specific features of the target protein specific dataset and design new chemical molecules, wherein the pre-trained generative model is obtained by: obtaining an input dataset comprising molecules in a pre-defined format and training a generative model with the input dataset to obtain the pre-trained generative model, and the target protein specific dataset (TPSD) is a curated target protein specific dataset (CTPSD) obtained by:

obtaining a plurality of other proteins having one or more properties similar to one or more corresponding properties of the target protein; and iteratively applying a reinforcement learning (RL) technique on the target-specific generative model and a predictive model to obtain a set of target-specific small molecules, wherein each target-specific small molecule from the set of target-specific small molecules comprises one or more associated physico-chemical properties and the one or more associated physico-chemical properties comprise a Synthetic Accessibility Score (SAS), a biological activity, a partition co-efficient (log P), a molecular weight, and the docking score, and the predictive model is pre-trained using a protein dataset, and the predictive model predicts the one or more associated physico-chemical properties for each target-specific small molecule from the set of target-specific small molecules, and the RL technique (i) obtains the set of target-specific small molecules based on a reward assigned to the target-specific generative model and (ii) increases binding affinity of the set of target-specific small molecules based on the reward assigned to the target-specific generative model, and the reward is used to optimize the target-specific generative model iteratively using a regularized reward function, and the target-specific generative model is subjected to the docking score optimization with the predictive model using a regularized reinforcement learning (RL) technique, and wherein the regularized reward function comprises:

$$r(x) = \exp\left(\frac{-x}{3.0}\right)$$

where x is a docking score from the predictive model and r (x) is the reward for reinforcing the target-specific generative model;

applying physico-chemical property filters on each target-specific small molecule from the set of target-specific small molecules to obtain a reduced set of target-specific molecules, wherein the physico-chemical property filters relate to an octanol-water partition coefficient (log P), a molecular weight (MW) and the synthetic accessibility score (SAS) associated with each target-specific small molecule, wherein the SAS avoids molecules which are difficult to synthesize, and each molecule from the reduced set of target-specific molecules comprises one or more desired physico-chemical properties, and small molecules are docked at an active site of the target protein are chosen to curate a target specific training dataset and molecules with high virtual screening scores ($<=-7.0$) are chosen to form a final target-specific small molecule dataset for transfer learning;

performing a virtual screening of the reduced set of target-specific molecules against the target protein to obtain a screened set of target-specific molecules, the screened set of target-specific molecules serve as one or more potential inhibitors of the target protein; and validating the screened set of target-specific molecules by comparing the screened set of target-specific molecules with a dataset of target-specific small molecules set aside for validation, wherein selective and diverse small molecules similar to the dataset of the target-specific small molecules are generated using the target-specific generative model by optimizing affinity of the small molecules towards the target protein by utilizing inhibitors of proteins with similar active site, thereby reproducing the existing target-specific small molecules from a validation dataset.

6. The non-transitory computer readable medium of claim 5, wherein the CTPSD comprises at least a subset of the plurality of other proteins, and wherein each protein from the subset of the plurality of other proteins comprises one or more small molecules.

* * * * *